US009668638B2

(12) United States Patent
Nimkar et al.

(10) Patent No.: US 9,668,638 B2
(45) Date of Patent: Jun. 6, 2017

(54) BALLOON SYSTEM INCLUDING REGISTRATION MARKING

(71) Applicant: NinePoint Medical, Inc., Cambridge, MA (US)

(72) Inventors: Shekhar Nimkar, Swampscott, MA (US); David Vader, Brookline, MA (US); Jim Houskeeper, Mendon, MA (US)

(73) Assignee: Ninepoint Medical Inc., Cambridge, MA (US)

( * ) Notice: Subject to any disclaimer, the term of this patent is extended or adjusted under 35 U.S.C. 154(b) by 194 days.

(21) Appl. No.: 14/172,569

(22) Filed: Feb. 4, 2014

(65) Prior Publication Data

US 2014/0228636 A1 Aug. 14, 2014

Related U.S. Application Data

(60) Provisional application No. 61/762,466, filed on Feb. 8, 2013.

(51) Int. Cl.
*A61B 1/04* (2006.01)
*A61B 1/00* (2006.01)
*A61B 5/00* (2006.01)

(52) U.S. Cl.
CPC ........ *A61B 1/00009* (2013.01); *A61B 1/0005* (2013.01); *A61B 5/0066* (2013.01); *A61B 5/6852* (2013.01); *A61B 5/6853* (2013.01)

(58) Field of Classification Search
CPC ...... A61B 1/05; A61B 1/00082; A61B 1/0125
(Continued)

(56) References Cited

U.S. PATENT DOCUMENTS

2006/0004323 A1* 1/2006 Chang ................ A61B 17/24
604/28
2009/0259296 A1 10/2009 McIff et al.
(Continued)

FOREIGN PATENT DOCUMENTS

WO WO2008086613 A1 7/2008

OTHER PUBLICATIONS

International Search Report and Written Opinion of PCT/US14/14673 filed Feb. 4, 2014, by International Search Authority dated Apr. 21, 2014.
(Continued)

*Primary Examiner* — Timothy J Neal
(74) *Attorney, Agent, or Firm* — Sorell Lenna & Schmidt, LLP

(57) ABSTRACT

A system for registering images is provided. The system includes a first imaging device having an imager positioned at a distal end thereof. The first image device is configured to produce a first image of a body cavity. The system includes an imaging system having a second imaging device having an imager positioned at a distal end thereof and configured to be positioned approximate to said imager of said first imaging device within said body cavity and configured to produce a second image. An elongated member having an outer surface is molded to include imaging markers such that said imaging markers are embedded within the outer surface. At least one of the image markers is configured to produce registration information in the first image and the second image.

20 Claims, 10 Drawing Sheets

(58) Field of Classification Search
USPC .................................. 600/104, 109, 113, 114
See application file for complete search history.

(56) References Cited

U.S. PATENT DOCUMENTS

2010/0041949 A1  2/2010  Tolkowsky
2013/0204126 A1  8/2013  Namati et al.

OTHER PUBLICATIONS

Notification Concerning Transmittal of International Preliminary Report on Patentability (Chapter I of the Patent Cooperation Treaty) (PCT Rule 44bis.l(c)) Date of mailing Aug. 20, 2015 (Aug. 20, 2015) International application No. PCT/US2014/014673 The International Bureau transmits herewith the international preliminary report on patentability (Chapter I of the Patent Cooperation Treaty). International Preliminary Report on Patentability, PCT/US2014/014673,3. This report contains indications relating to the following items: Box No. I—Basis of the report; Box No. V—Reasoned statement under Article 35(2) with regard to novelty, inventive step or industrial applicability; citations amd explanations supporting such statement; Box No. VI—Certain documents cited.

\* cited by examiner

… (1/2)

BALLOON SYSTEM INCLUDING REGISTRATION MARKING

RELATED APPLICATIONS

This application claims priority to the U.S. Provisional Application Ser. No. 61/762,466 filed Feb. 8, 2013, which is incorporated herein by reference, in its entirety.

TECHNICAL FIELD

The present disclosure generally relates to medical devices, systems and methods for imaging in biomedical and other medical and non-medical applications including balloon systems with registration markers and methods of producing the same.

BACKGROUND

Various forms of imaging systems are used in healthcare to produce images of a patient. In some instances, multiple images are taken of a particular portion of a patient's anatomy, for example, by one or more device including, for example, balloon catheters having visual markers. The visual markers function as registration markers to orient each image in a common frame of reference, for example. This disclosure describes an improvement over these prior art technologies.

SUMMARY

An imaging system is provided in accordance with the principles of the present disclosure that includes a first imaging device having an imager positioned at a distal end thereof. The first imaging device is configured to produce a first image of a body cavity. An imaging system includes a second imaging device having an imager positioned at a distal end thereof and configured to be positioned approximate to the imager of the first imaging device within the body cavity and to produce a second image. An elongated member includes an outer surface. The elongated member is molded to include imaging markers such that the imaging markers are embedded within the outer surface. At least one of the image markers is configured to produce registration information in the first image and the second image.

In one embodiment, in accordance with the principles of the present disclosure a system for registering images is provided. The system includes a first imaging device having an imager positioned at a distal end thereof. The first image device is configured to produce a first image of a body cavity. An imaging system includes a second imaging device having an imager positioned at a distal end thereof and configured to be positioned approximate to the imager of the first imaging device within the body cavity and to produce a second image. An elongated member has an outer surface defining a non-uniform profile. The outer surface includes at least one surface feature such that the profile is non-uniform. The surface feature is viewable in the first image and the second image to produce registration information.

In one embodiment, in accordance with the principles of the present disclosure a method for registering images in a system having a first imaging device configured to produce a first image and an imaging system including a second imaging device molded into a surface of an elongated member is provided wherein the second imaging device is rotatable and configured to produce a second image. The method includes inserting said first imaging device into a cavity of a patient; inserting said imaging system positioned with said elongated member into the cavity of the patient; producing by said first imaging device a first image containing an image of at least one marker; producing by said second imaging device a second image containing an image of said marker; and registering said first image and said second image based on the image of the marker in the first and second images.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
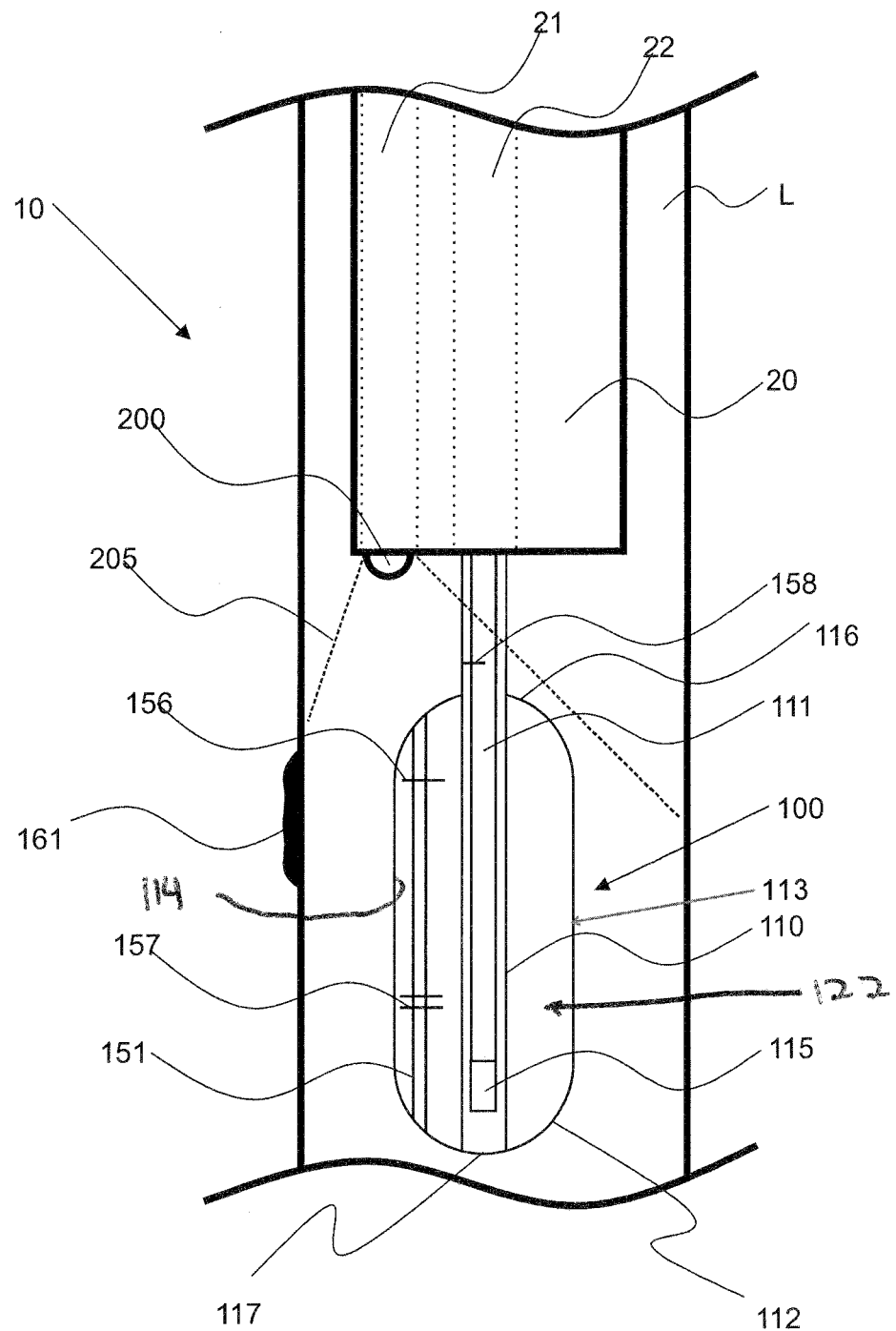
FIG. 1 is a side view of components of an imaging system, in accordance with the principles of the present disclosure.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

In one embodiment, a stripe is extruded in the parison of the blow mold used for making an expandable elongated member, such as, for example a catheter and/or balloon for use in optical coherence tomography (OCT) or another imaging technique. The stripe is configured to act as a registration marker to orient multiple images in a common frame of reference, for example. In some embodiments, the stripe is extruded in the parison that is used to form the balloon/catheter such that the stripe is embedded in a wall that defines the balloon/catheter. In some embodiments, the stripe is embedded in a wall that defines the balloon/catheter such that the stripe does not protrude through the inner and outer surfaces of the wall that defines the balloon and the stripe is embedded in the thickness of the wall. In some embodiments, the stripe is anti-reflective. In some embodiments, the stripe is radiopaque. In some embodiments, the stripe comprises polyethylene terephthalate (PET), such as, for example, black PET. In some embodiments, the stripe is formed using high temperature ink with a pad print method.

The following discussion includes a description of an imaging system and related methods of employing the imaging system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of an imaging system, such as, for example, an imaging system 10 for producing multiple registered images of a body lumen.

FIG. 1 illustrates a side view of a distal portion of imaging system 10. Endoscope 20 is positioned into a body lumen L, such as, for example, the esophagus of a patient, for imaging using system 10.

The components of imaging system 10 can be fabricated from biologically acceptable materials suitable for medical applications, including metals, synthetic polymers, ceramics and bone material and/or their composites, depending on the particular application and/or preference of a medical practitioner. For example, the components of imaging system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys, ceramics and composites thereof, thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK, composites of PEEK, resorbable polymers and totally resorbable materials. Various components of imaging system 10 may have material composites, including the above materials, to achieve various desired characteristics such as strength, rigidity, elasticity, compliance, biomechanical performance, durability and radiolucency or imaging preference. The components of imaging system 10, individually or collectively, may also be fabricated from a heterogeneous material such as a combination of two or more of the above-described materials. The components of imaging system 10 may be monolithically formed, integrally connected or include fastening elements and/or instruments, as described herein.

System 10 includes a first imaging device, such as, for example a camera 200 and an endoscope 20. In some embodiments, camera 200 is integrally formed with endoscope 20 such that camera 200 is permanently fixed to endoscope 20. In some embodiments, camera 200 is fixedly attached to a distal portion of endoscope 20, with wires or other conduits traveling proximally to one or more image display devices, not shown but typical to endoscopic visualization systems. In some embodiments, camera 200 includes an elongate shaft that is slidingly received by endoscope 20, such as, for example, a working channel 21 defined by an inner surface of endoscope 20. This configuration allows camera 200 to be moved axially within working channel 21 to position a lens of camera 200 as desired by a medical practitioner for purposes of imaging or otherwise. In some embodiments, camera 200 forms a friction fit with the inner surface that defines working channel 21 to fix camera 200 axially within working channel 21. In some embodiments, camera 200 can be variously connected with endoscope 20, such as, for example, monolithic, integral connection, frictional engagement, threaded engagement, mutual grooves, screws, adhesive, nails, barbs and/or raised element. In some embodiments, camera 200 is a visible light camera. In some embodiments, camera 200 is a stereoscopic camera.

System 10 further includes a second imaging device, such as, for example, an optical coherence tomography (OCT) device 100. OCT device 100 includes an elongate shaft 110, which is slidingly disposed in a working channel 22 of endoscope 20 defined by a second inner surface of endoscope 20. Working channel 21 is spaced apart from working channel 22. In some embodiments, working channel 22 is coaxial with a longitudinal axis defined by endoscope 20 and working channel 21 is offset from the longitudinal axis defined by endoscope 20.

OCT device 100 includes balloon 112 having a proximal end 116 and a distal end 117. Balloon 112 is movable between a collapsed or unexpanded configuration to an inflated or expanded configuration by delivering an inflation material, such as for example, a gas or fluid into a cavity 122 of balloon 112 defined by an inner surface 114 of balloon 112. Balloon 112 is shown in 112 in a partially inflated state. In some embodiments, balloon 112 is made from a resilient biocompatible material. In one embodiment, balloon 112 is a compliant balloon that resists stretching. In one embodiment, balloon 112 comprises polyolefin copolymer (POC). In one embodiment, balloon 112 is a non-compliant balloon that stretches, at least to some degree. In one embodiment, balloon 112 comprises polyethylene terapthelate (PET). In some embodiments, balloon 112 can have various cross section configurations, in the collapsed or unexpanded configuration and/or the inflated or expanded configuration, such as, for example, oval, oblong, triangular, rectangular, square, polygonal, irregular, uniform, non-uniform, variable, tubular and/or tapered. In some embodiments, outer surface 113 may have various surface configurations, such as, for example, smooth and/or surface configurations to enhance fixation with tissue that defines lumen L, such as, for example, rough, arcuate, undulating, porous, semi-porous, dimpled, polished and/or textured.

Balloon 112 can be a single or a multi-layered balloon, where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation. In some embodiments, balloon 112 is a multi-layer balloon, wherein at least one registration marker is disposed between two of the layers, as will be discussed. In some instances, it will be apparent that one can vary size, material, and/or orientation to at least some degree. Balloon 112 can be adapted to withstand the particular stresses, pressures, and deformities to which balloon 112 might be placed under when inflated within lumen L.

Balloon 112 is defined by a wall 107 including inner surface 114 and an outer surface 113 opposite inner surface 114. Cavity 122 is configured for disposal of an inflation material, such as for example, air or saline, to move balloon 112 between the collapsed or unexpanded configuration and the inflated or expanded configuration. In some embodiments, wall 107 is a single layer such that there is no space or gap between inner surface 114 and outer surface 113 and wall 107 includes at least one registration marker, such as, for example, at least one of registration markers 151 and 156-158 embedded therein such that the registration marker does not extend through inner surface 114 or outer surface 113.

Registration markers 151 and 156-158 are positioned to be viewed by camera 200 and/or OCT device 100, which are included in images produced by camera 200 and/or the two-dimensional or three-dimensional images produce by OCT device 100. In some embodiments, registration markers 151 and 156-158 each comprise a material that is different than the material that forms wall 107. Each of the registration markers is configured to provide a reference point which can be identified in separate images. This allows the registration markers to orient each of the separate images in a common frame of reference, for example. In some embodiments, at least one of registration markers 151 and 156-158 comprises a radiopaque material, such as, for example PET. In some embodiments, wall 107 comprises a transparent material and at least one of registration markers 151 and 156-158 comprises a radiopaque material, such as, for example black PET to provide sufficient contrast.

In some embodiments, at least one of registration markers 151, 156, 157 and 158 comprises material that is configured to absorb, reflect and/or scatter one or more forms of electromagnetic radiation. In one embodiment, one or more markers 151, 156, 157 and 158 are reflective and/or absorptive to visible light, such as visible light used by camera 200. In some embodiments, one or more markers 151, 156, 157 and 158 are reflective and/or absorptive to infrared light, such as infrared light used by OCT device 100. In some embodiments, markers 151, 156, 157 and 158 are configured to scatter light, such as visible or infrared light. In some embodiments, markers 151, 156, 157 and 158 include one or more components such as, for example a wire (e.g. a 20-30 micron wire), a metal foil, a metal strip, an ink, a dye, and/or combinations of thereof. In some embodiments, markers 151, 156, 157 and 158 may absorb, reflect and/or scatter ultrasound. In some embodiments, markers 151, 156, 157 and 158 may include one or more projections, geometric shapes or other identifiable structures that are imagable by system 10 and/or modify the shape of something visible to system 10.

In some embodiments, balloon 112 is manufactured by extruding a strip or stripe of material to form registration marker 151 and/or 156-158 in the parison of the mold such that registration markers 151 and 156-158 are embedded in wall 107 between inner surface 114 and outer surface 113. That is, registration markers 151 and 156-158 are embedded in wall 107 such that registration markers 151 and 156-158 do not extend through inner surface 114 or outer surface 113. Balloon 112 is blow molded to the required dimension and size with markers 151 and/or 156-158 already embedded in wall 107. In one embodiment, a high temperature ink and pad print is disposed in the parison to create registration markers 151 and 156-158 in wall 107. In some embodiments, at least one of registration markers 151 and 156-158 is embedded in wall 107 such that at least one of registration markers 151 and 156-158 extends through inner surface 114 without extending through outer surface 113. In some embodiments, at least one of registration marker 151 and 156-158 is embedded in wall 107 such that at least one of registration marker 151 and 156-158 extends through outer surface 113 without extending through inner surface 114.

As shown in FIG. 1, registration markers 156-158 are strips or a pair of parallel strips of material that each extend perpendicular to an axis defined by shaft 110 and registration marker 151 is a strip or pair of parallel strips of material that each extend perpendicular to the axis defined by shaft 110. In some embodiments, at least one of registration markers 151 and 156-158 is variously shaped, such as, for example, linear, non-linear, wavy, zig zag, oval, oblong, triangular, square, polygonal, irregular, uniform, non-uniform, offset, staggered, undulating, arcuate, variable and/or tapered. In some embodiments, at least one of registration markers 151 and 156-158 may be disposed at alternate orientations, relative to the axis defined by shaft 110, such as, for example, transverse, perpendicular and/or other angular orientations such as acute or obtuse, co-axial and/or may be offset or staggered. In some embodiments, registration markers 156-158 each comprise one or a plurality of strips of material.

In some embodiments, at least one of registration markers 151 and 156-158 is disposed on inner surface 114 such that at least one of registration markers 151 and 156-158 is disposed in cavity 122 and is spaced apart from outer surface 113 by wall 107. That is, an outer surface of at least one of registration markers 151 and 156-158 engages inner surface 114. In some embodiments, at least one of registration markers 151 and 156-158 is disposed on outer surface 113 such that at least one of registration markers 151 and 156-158 is spaced apart from inner surface 114 and/or cavity 122 by wall 107. That is, an outer surface of at least one of registration markers 151 and 156-158 engages outer surface 113. In some embodiments, at least one of registration markers 151 and 156-158 is disposed on inner surface 114 such that at least one of registration markers 151 and 156-158 is disposed in cavity 122 and is spaced apart from outer surface 113 by wall 107 and at least one of registration markers 151 and 156-158 is disposed on outer surface 113 such that at least one of registration markers 151 and 156-158 is spaced apart from inner surface 114 and/or cavity 122 by wall 107.

In some embodiments, marker 151 comprises one or more strips of material oriented parallel to a longitudinal axis of balloon 112, as shown in FIG. 1. Marker 151 is typically positioned to be viewed in each 360° rotation of an imaging assembly 115, such as to be included in each cross sectional image of lumen L produced by OCT device 100. Marker 151 is typically further positioned to be viewed by camera 200, such that images created by camera 200 can be radially or otherwise registered with images created by OCT device 100. In one embodiment, marker 151 wraps around the proximal end 116 of balloon 112 such as to be viewed by camera 200, while being axially aligned with the major axis of balloon 112. In some embodiments, multiple markers are placed along a circumference of balloon 112, such as, for example, one or more markers positioned approximately 180° from marker 151, such as to register images and/or to determine variations in angular velocity of imaging assembly 115, such as to reduce non-uniform rotational distortion (NURD).

In some embodiments, markers 156 and 157 are oriented along a partial circumference of balloon 112, as shown in FIG. 1. In some embodiments, markers 156, 157 are positioned to be viewed by imaging assembly 115 when imaging assembly 115 is at pre-determined longitudinal positions, such as, for example, during a translation when OCT device 100 is configured to produce three-dimensional images of lumen L. Images including representations of markers 156 and/or 157 may be correlated to the specific locations of balloon 112 to which they are positioned, such as to provide longitudinal registration information for one or more images produced by OCT device 100. Further longitudinal image registration can be performed by correlating a second image created subsequent to a first image, wherein the first image includes a representation of markers 156 and/or 157, and the longitudinal position of the second image is determined by accounting for translational velocity of imaging assembly 115. For example, if an inner member 111 disposed within shaft 110 and/or cavity 122 and imaging assembly 115 translate at 0.5 mm/sec, a second image produced 3 seconds from a first image including the distal end of registration marker 156 will comprise an image 1.5 mm from the distal end of registration marker 156.

In some embodiments, registration marker 158 is positioned to be visible by camera 200. Marker 158 is positioned with known radial and longitudinal offsets to markers 151, 156 and/or 157, such that images produced by camera 200 can be radially, longitudinally or otherwise registered to images produced by OCT device 100 that include representations of markers 151, 156 and/or 157. Alternatively or additionally, marker 158 can be used to longitudinally position balloon 112, such as manually or automatically through the geometric position detection of marker 158 from images provided by camera 200. In a particular embodiment, camera 200 comprises a stereoscopic camera, such as the stereoscopic camera described with reference to FIG. 5 and the depth information provided by the stereoscopic image correlates to marker 158, and thus balloon 112 and its distance from the distal end of camera 200 and/or endoscope 20.

The registration markers of system 10 may be one or more integral components to the system, such as registration markers 151, 156, 157 and 158, or the registration marker may comprise an anatomical landmark, such as a vessel or tissue mark 161. In some embodiments, tissue mark 161 may be created by system 10. Mark 161 can include dyed tissue, tissue modified to reflect light, tissue modified to absorb light, tissue modified to scatter light, tissue modified by energy such as tissue scarred by laser energy delivered by OCT device 100, tissue proximate biopsied or other removed tissue, tissue mark in tissue, an implant such as a removable tissue implant such as a removable implanted filament placed through endoscope 20, and various combinations thereof.

Tissue marker 161, pre-existing in lumen L or created by a device or assembly of system 10 as is described hereinabove, may be used to radially, longitudinally or otherwise register one or more images produced by system 10. Camera 200 may create one or more images including representations of tissue marker 161 such as when balloon 112 is deflated or partially inflated. OCT device 100 may produce one or more images including a representation of tissue marker 161, such as when balloon 112 is inflated and imaging assembly 115 is longitudinally aligned with at least a portion of tissue marker 161.

In some embodiments, balloon 112 includes multiple layers of material. For example in one embodiment, inner surface 114 defines a first layer of material and outer surface 113 defines a second layer of material that is separable from the first layer of material. In such embodiments, at least one of registration markers 151, 156, 157 and 158 is disposed between the first layer and the second layer such that the registration marker does not extend through inner surface 114 or outer surface 113. In some embodiments, balloon 112 includes one or a plurality of layers.

In some embodiments, balloon 112 is pre-formed to include at least one distinct surface configuration 162 configured to act similar to registration markers 151, 156, 157, 158 and 161 to provide a reference point which can be identified in separate images to orient each of the separate images in a common frame of reference, for example. That is, surface configuration 162 imparts an outer diameter of balloon 112 with a non-uniform cross sectional configuration such that surface configuration 162 in one image can be matched with surface configuration 162 in a second image to orient the first image relative to the second image. In some embodiments, surface configuration 162 extends along all or only a portion of a length of balloon defined by a distance between proximal end 116 and distal end 117.

Figure 7:
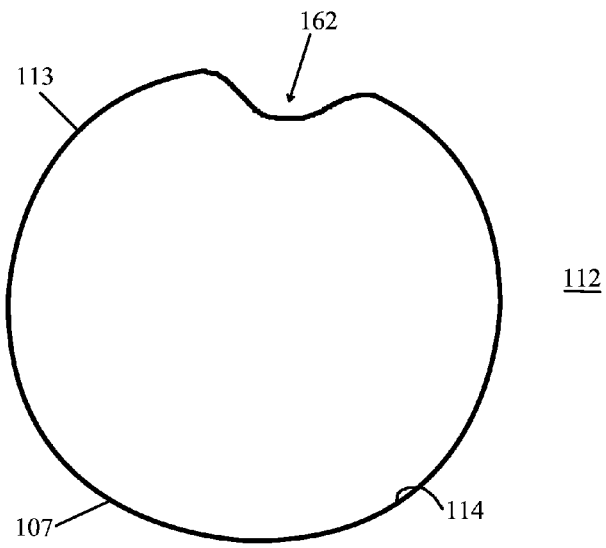
FIG. 7 is a cross sectional view of one embodiment of a component of the system shown in FIG. 1.
Figure 8:
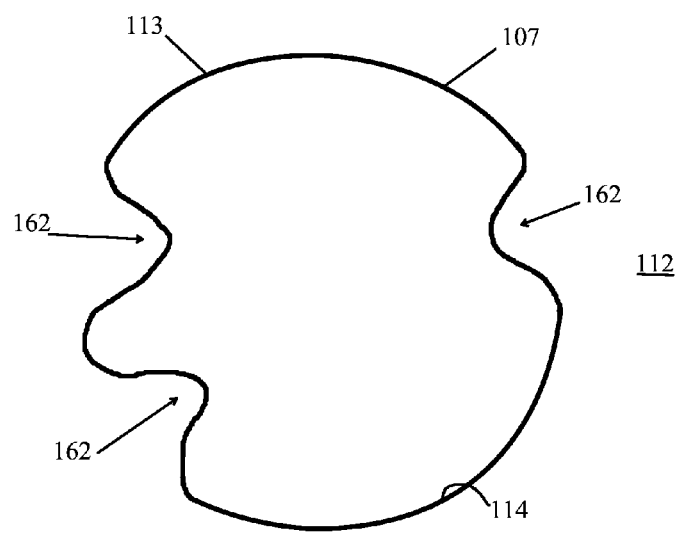
FIG. 8 is a cross sectional view of one embodiment of a component of the system shown in FIG. 1.

In one embodiment, surface configuration 162 is a recess or cavity that extends into outer surface 113 to provide the outer diameter of balloon 112 with a non-uniform and non-circular cross sectional configuration when balloon 112 is in an inflated or expanded configuration, as shown in FIG. 7. In one embodiment, surface configuration 162 is a plurality of spaced apart recesses or cavities that each extend into outer surface 113 to provide the outer diameter of balloon 112 with a non-uniform and non-circular cross sectional configuration when balloon 112 is in an inflated or expanded configuration, as shown in FIG. 8. In some embodiments, at least one of recesses 162 each has a width of 0.004 inches to 0.005 inches when balloon 112 is in the expanded configuration. In some embodiments, at least one of recesses 162 each has a depth of 0.004 inches to 0.005 inches when balloon 112 is in the expanded configuration.

Figure 9:
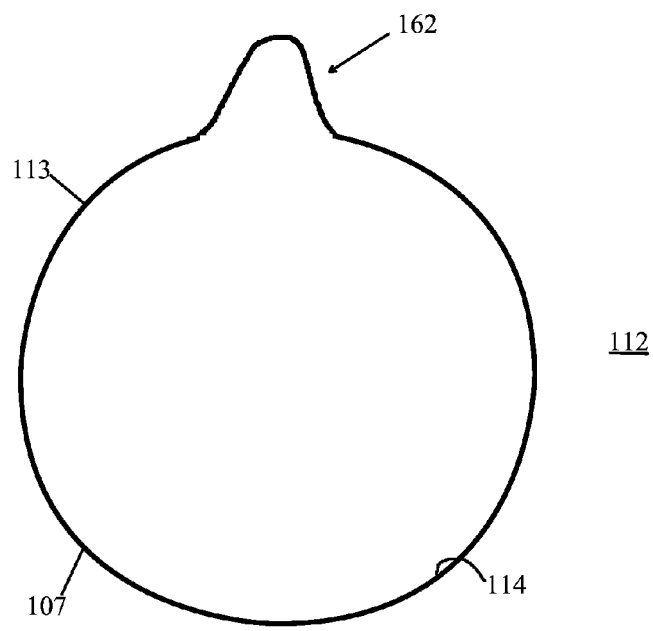
FIG. 9 is a cross sectional view of one embodiment of a component of the system shown in FIG. 1.
Figure 10:
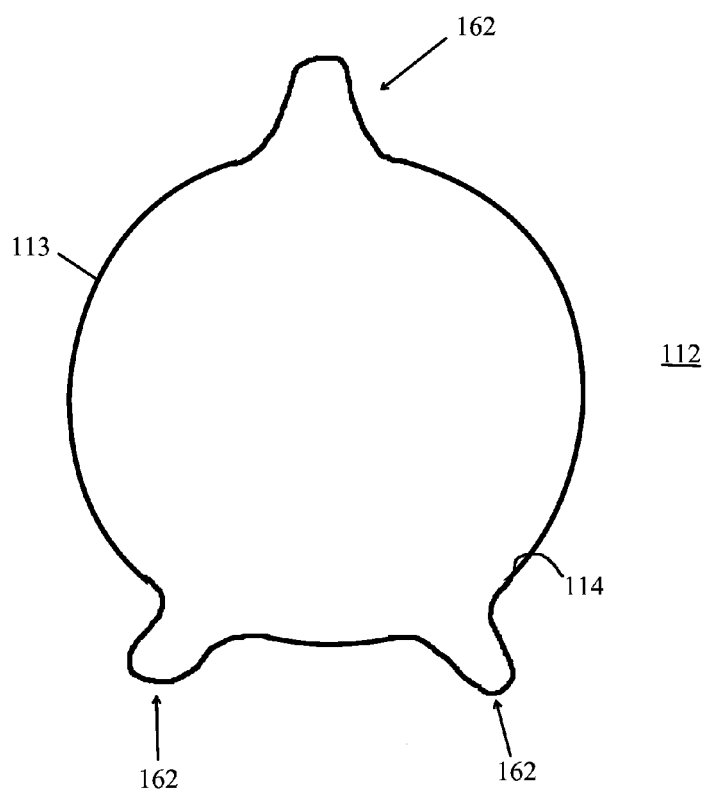
FIG. 10 is a cross sectional view of one embodiment of a component of the system shown in FIG. 1.

In one embodiment, surface configuration 162 is an outward projection that provides the outer diameter of balloon 112 with a non-uniform and non-circular cross sectional configuration when balloon 112 is in an inflated or expanded configuration, as shown in FIG. 9. In one embodiment, surface configuration 162 is a plurality of spaced apart projections that each extend outward to provide the outer diameter of balloon 112 with a non-uniform and non-circular cross sectional configuration when balloon 112 is in an inflated or expanded configuration, as shown in FIG. 10.

In some embodiments, wall 107 may have a uniform thickness in at least one of the embodiments shown in FIGS. 7-10, the thickness of wall 107 being defined by a distance between inner surface 114 and outer surface 113. In some embodiments, the thickness of wall 107 varies in at least one of the embodiments shown in FIGS. 7-10 to define surface configuration 162. In some embodiments, all or only a portion of surface configuration 162 may be variously configured and dimensioned, such as, for example, planar, concave, polygonal, irregular, uniform, non-uniform, staggered, tapered, consistent or variable.

Figure 11:
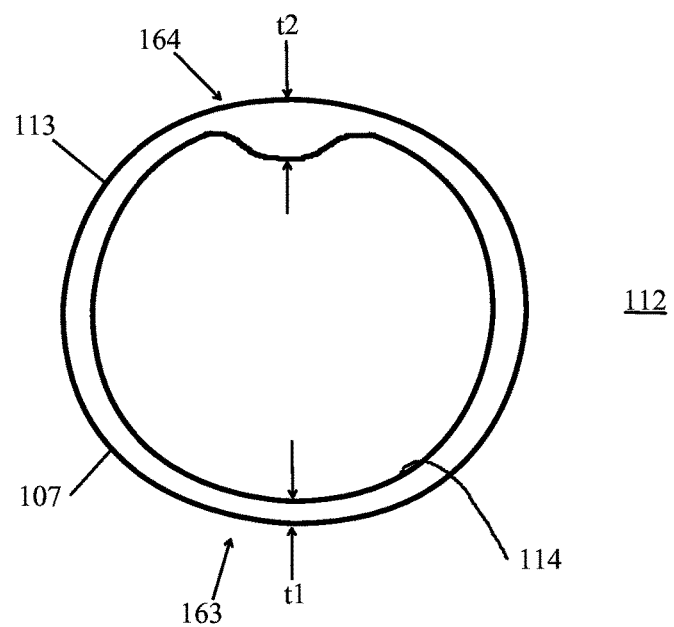
FIG. 11 is a cross sectional view of one embodiment of a component of the system shown in FIG. 1.

In some embodiments, balloon 112 is pre-formed such that the thickness of wall 107 is non-uniform, as shown in FIG. 11. That is, in such embodiments, wall 107 includes a first portion 163 having a first thickness t1 and a second portion 164 including a second thickness t2 that is greater than first thickness t1. Second portion 164 acts similar to registration markers 151, 156, 157, 158 and 161 and surface configuration 162 to provide a reference point which can be identified in separate images to orient each of the separate images in a common frame of reference, for example. That is, second portion 164 imparts wall 107 with a non-uniform thickness, while providing balloon 112 with an outer diameter having uniform cross sectional configuration such that surface configuration 162 in one image can be matched with second portion 164 in a second image to orient the first image relative to the second image. In some embodiments, second portion 164 extends along all or only a portion of the length of balloon defined by the distance between proximal end 116 and distal end 117.

Figure 12:
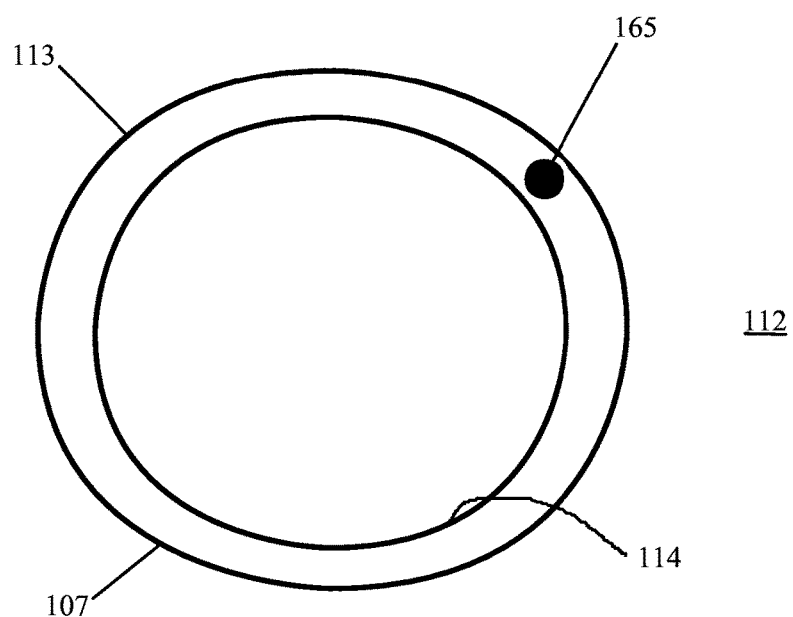
FIG. 12 is a cross sectional view of one embodiment of a component of the system shown in FIG. 1.

In some embodiments, wall 107 includes at least one fiber embedded therein, such as, for example, at least one photovoltaic fiber 165 positioned between inner surface 114 and outer surface 113 such that fiber 165 does not extend through inner surface 114 or outer surface 113, as shown in FIG. 12. In some embodiments, fiber 165 is positioned equidistant between inner surface 114 and outer surface 113. In some embodiments, fiber 165 is positioned to be closer to one of inner surface 114 or outer surface 113. In some embodiments, fiber 165 extends parallel to a longitudinal axis defined by balloon 112. In some embodiments, fiber 165 may be disposed at alternate orientations, relative to the longitudinal axis defined by balloon 112, such as, for example, transverse, perpendicular and/or other angular orientations such as acute or obtuse, co-axial and/or may be offset or staggered.

Fiber 165 acts similar to registration markers 151, 156, 157, 158 and 161, surface configuration 162 and second portion 164 to provide a reference point which can be identified in separate images to orient each of the separate images in a common frame of reference, for example. That is, fiber 165 is detectable by an optical frequency domain imaging (OFDI) laser as photons from the laser result in an increased signal with an increased voltage at the end of fiber 165. The signal is detected and used to determine the angular orientation of balloon 112, for example.

Markers 151, 156, 157, 158 and 161, surface configuration 162, second portion 164 and fiber 165 may be used singly or in combination to provide registration information between one or more images produced by system 10. In some embodiments, 151, 156, 157, 158 and 161, surface configuration 162, second portion 164 and fiber 165 may be used singly or in combination to position (e.g. to advance, retract and/or rotate) one or more components of system 10, such as OCT device 100 and/or camera 200. Markers 151, 156, 157 and/or 158 portion 164 and/or fiber 165 may be positioned at known radial and/or longitudinal offsets, such that when viewed in one or more images, the known offset provides registration and/or other data. Markers 151, 156, 157 and/or 158 portion 164 and/or fiber 165 may be constructed and arranged to provide registration data of a first image to a second image, registration data of a first image to a component of system 10 and/or registration data of a first image to a portion of a patient's anatomy.

Shaft 110 slidingly receives inner member 111. In some embodiments, inner member 111 is a fiber optic cable configured to transmit light energy. On the distal portion of inner member 111 is mounted imaging assembly 115. In some embodiments, imaging assembly 115 comprises mirrors, lenses, filters and/or prisms. In some embodiments, imaging assembly 115 is constructed and arranged to produce at least a two-dimensional cross sectional image of lumen L. In some embodiments, OCT device 100 is constructed and arranged to produce a three-dimensional reconstructed image of lumen L, such as by both rotating and translating imaging assembly 115, such as, for example, by rotating and translating inner member 111 via a rotating and translating assembly, not shown, but typically located at or about a proximal end of endoscope 20. In some embodiments, imaging assembly 115 can be rotated using a rotating motor positioned at the distal end of inner member 111, and translated using proximal advancement and pullback. Multiple cross-sectional "slices" can be combined into a three-dimensional image. The slices may comprises helical slices, such as when inner member 111 and imaging assembly 115 translate at a constant velocity, or they may be planar slices such as when inner member 111 and imaging assembly 115 translate after, but not during, each 360° revolution of inner member 111 and imaging assembly 115 (e.g. in a step-wise fashion), or other combinations thereof.

In some embodiments, a shaft or catheter having a closed end can be used instead of balloon 112 to contain and protect imaging assembly 115. It is envisioned that embodiments that use the shaft in place of balloon 112 may have registration markers and/or other identifiers similar to registration markers 151, 156, 157, 158 and 161, surface configuration 162, second portion 164 and fiber 165 to function and perform similar to registration markers 151, 156, 157, 158 and 161, surface configuration 162, second portion 164 and fiber 165. That is, registration markers 151, 156, 157, 158 and/or fiber 165 may be embedded in a wall of the shaft in the same manner as registration markers 151, 156, 157, 158 and/or fiber 165 are embedded in wall 107 of balloon 112. Likewise, the wall of the shaft can be formed to have a structure similar to second portion 164.

In operation and use, camera 200 with field of view 205 is positioned to provide end view images of lumen L. In some embodiments, camera 200 is selectively positioned within lumen L by moving endoscope 20 within lumen L and fixing endoscope 20 relative to lumen L. Balloon 112 and shaft 110 are advanced through working channel 22 in endoscope 20 while balloon 112 is in the compressed or uninflated configuration, such as prior to expansion and/or through the application of a vacuum. Balloon 112 is selectively positioned according to the preference of a medical practitioner to position imaging assembly 115 for imaging of lumen L.

A first image is produced by imaging assembly 115 or camera 200 and a second image is produced by either imaging assembly 115 or camera 200. The first image and second image each include registration data (e.g. images of at least one of registration markers 151, 156, 157, 158 and 161, surface configuration 162, second portion 164 and/or fiber 165). The first image and the second image can be registered based on this registration data. The registering can be performed automatically, such as by one or more algorithms included in system 10 and/or manually, such as by an operator of system 10. Registering of the first image to the second image can include radially registering by rotating one or both images to radially orient the images to each other or to a common frame of reference, longitudinally registering the images to each other or a common frame of reference, scaling the images such as enlarging or shrinking one or both images to similarly scale the images (e.g. similar scaling of image dimensions to actual anatomical dimensions), axially or radially correlating the images (e.g. provide information related to radial displacement, longitudinal displacement and/or scaling differences), and other combinations thereof.

Figure 2:
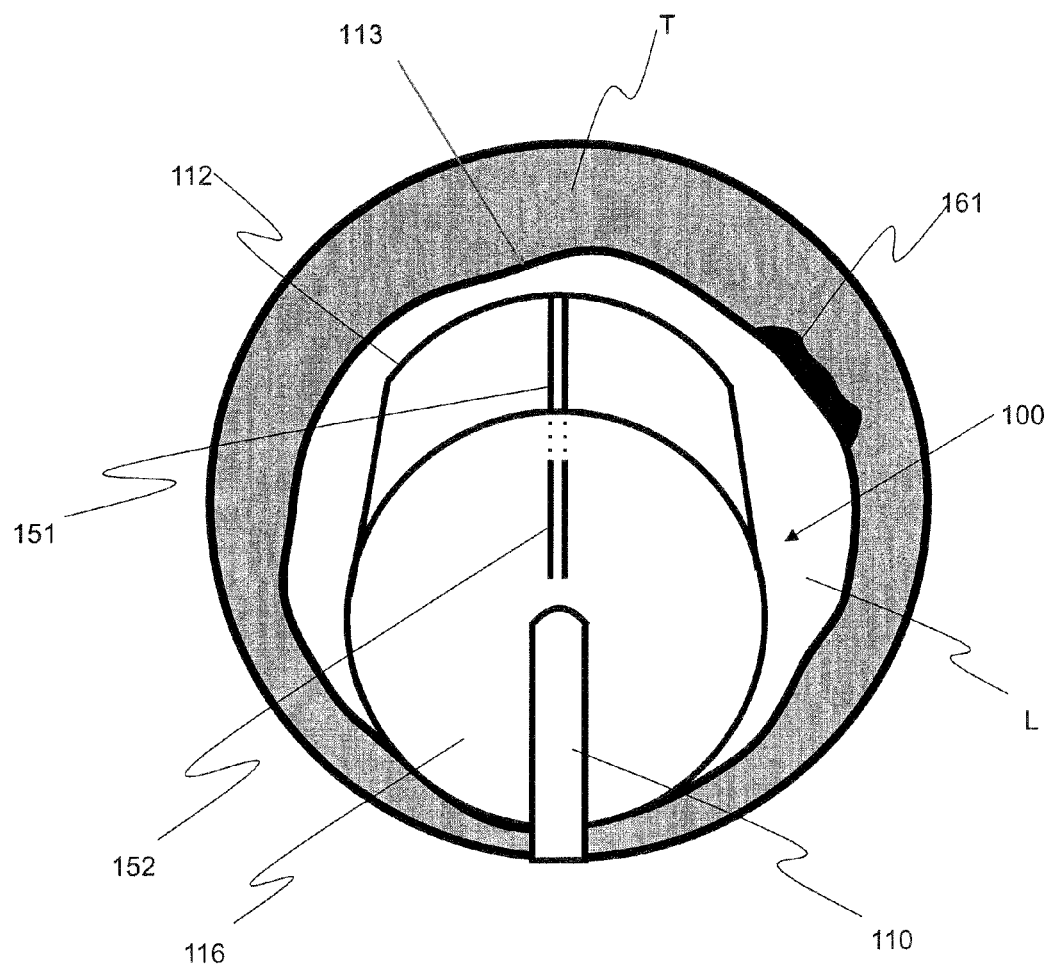
FIG. 2 is a representative drawing of an image produced by a component of the imaging system of FIG. 1.

The view image represented in FIG. 2 is a representative drawing of a typical image captured by camera 200 wherein balloon 112 includes registration marker 152 on proximal end 116 such that marker 152 is radially aligned with marker 151. In some embodiments, marker 152 and marker 151 comprise a single elongate marker that wraps around from the side of balloon 112 to its proximal end 116. With balloon 112 partially inflated, tissue marker 161 is visible to camera 200. After inflation of balloon 112, tissue marker 161 may be obscured by balloon 112. In these configurations, registration information may be collected by one or more images from camera 200, prior to full inflation of balloon 112.

Figure 3:
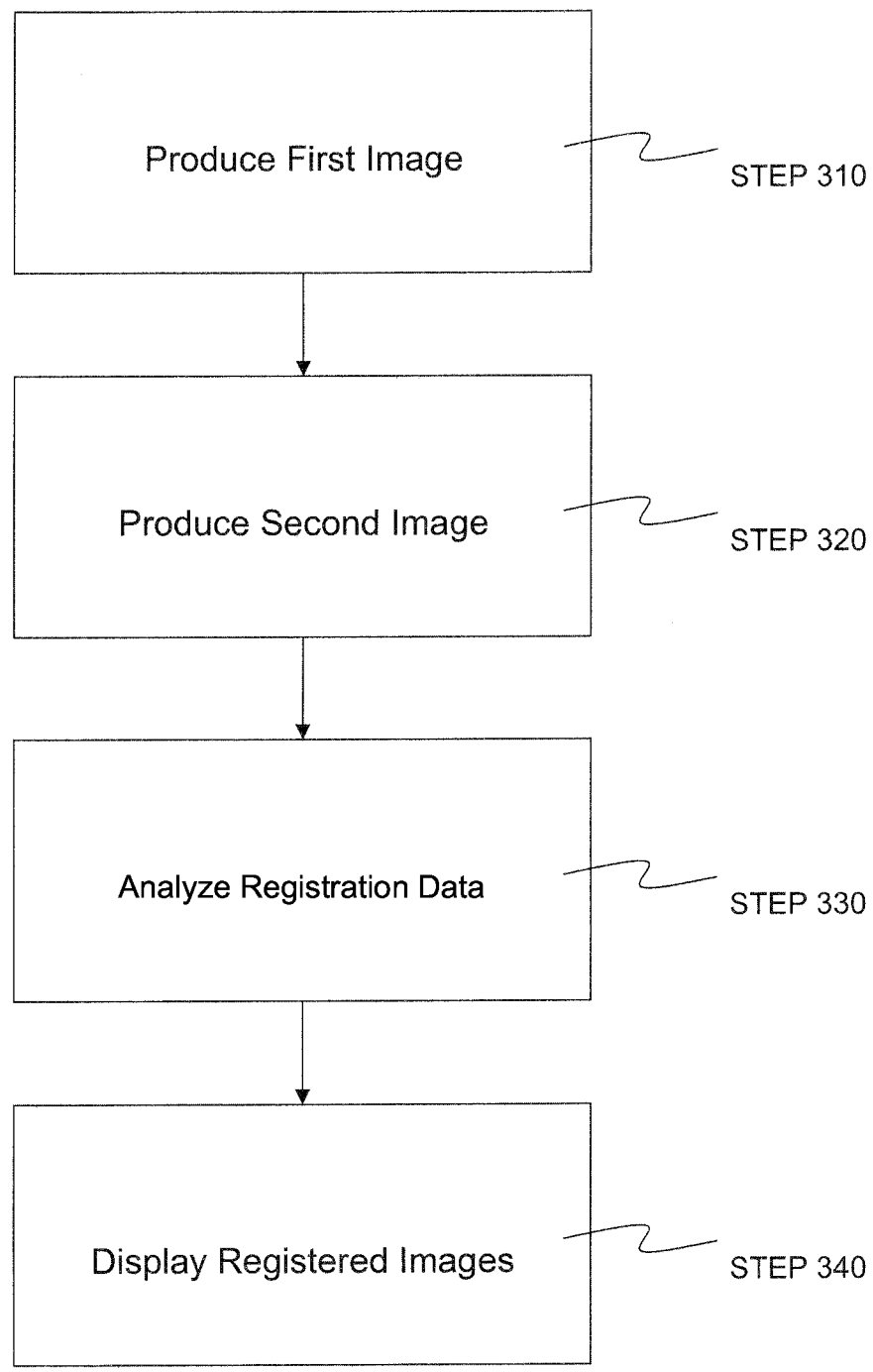
FIG. 3 is a flow chart of a method for producing registration data for multiple images, in accordance with the principles of the present disclosure.

A method for producing registration data for multiple images is shown in FIG. 3. In step 310, a first image is produced by a first imaging device, such as an image produced by camera 200. In step 320, a second image is produced by a second imaging device, such as OCT device 100. Alternatively, the first and second images can be produced by a single imaging device, such as two images produced by OCT device 100. The first and second images produced in steps 310 and 320 can be produced sequentially or simultaneously. The first and second images each include registration data, such as registration data correlating to representations of one or more registration markers, such as markers 151, 156, 157, 158 and/or 161 of system 10.

In step 330, registration data included in the first and second images is analyzed. In step 340, registration information is displayed, for example, on a video monitor. Registration information may include quantitative or other data representing angular or linear displacements between the first and second images. Registration information may include displaying the first and second images such that they are similarly oriented to the operator, the patient and/or another frame of reference. Registration information may include displaying the first image superimposed on the second image, with proper alignment. The registration information may include displaying a sub-portion of the first image superimposed on a full or partial second image.

A first image may comprise an end view image, such as, for example, the image shown in FIG. 2, such as an image produced by camera 200. The second image may comprises multiple cross-sectional images, or slices as described hereabove in reference to a three-dimensional imaging producing OCT device 100. The registration information may provide angular or longitudinal registration information between the first image and one or more of the second images, such as registration images between the first image and a three dimensional collection of slice images.

It is contemplated that in imaging system 10, an operator can rotate the display of the first image or the second image, in a manual, semi-automatic or fully automated mode. It is also contemplated that in the imaging system described herein, the system can manually or automatically rotate the first image and/or the second image to a known orientation, such as the same orientation as the patient being imaged, such as when the patient is positioned face up on an operating table, and the images are oriented such that anterior locations are positioned above posterior locations on a video monitor. Alternatively or additionally, registration information may include registration between a first image and a component of the imaging system and/or between a first image and a location in the patient's anatomy.

Figure 4:
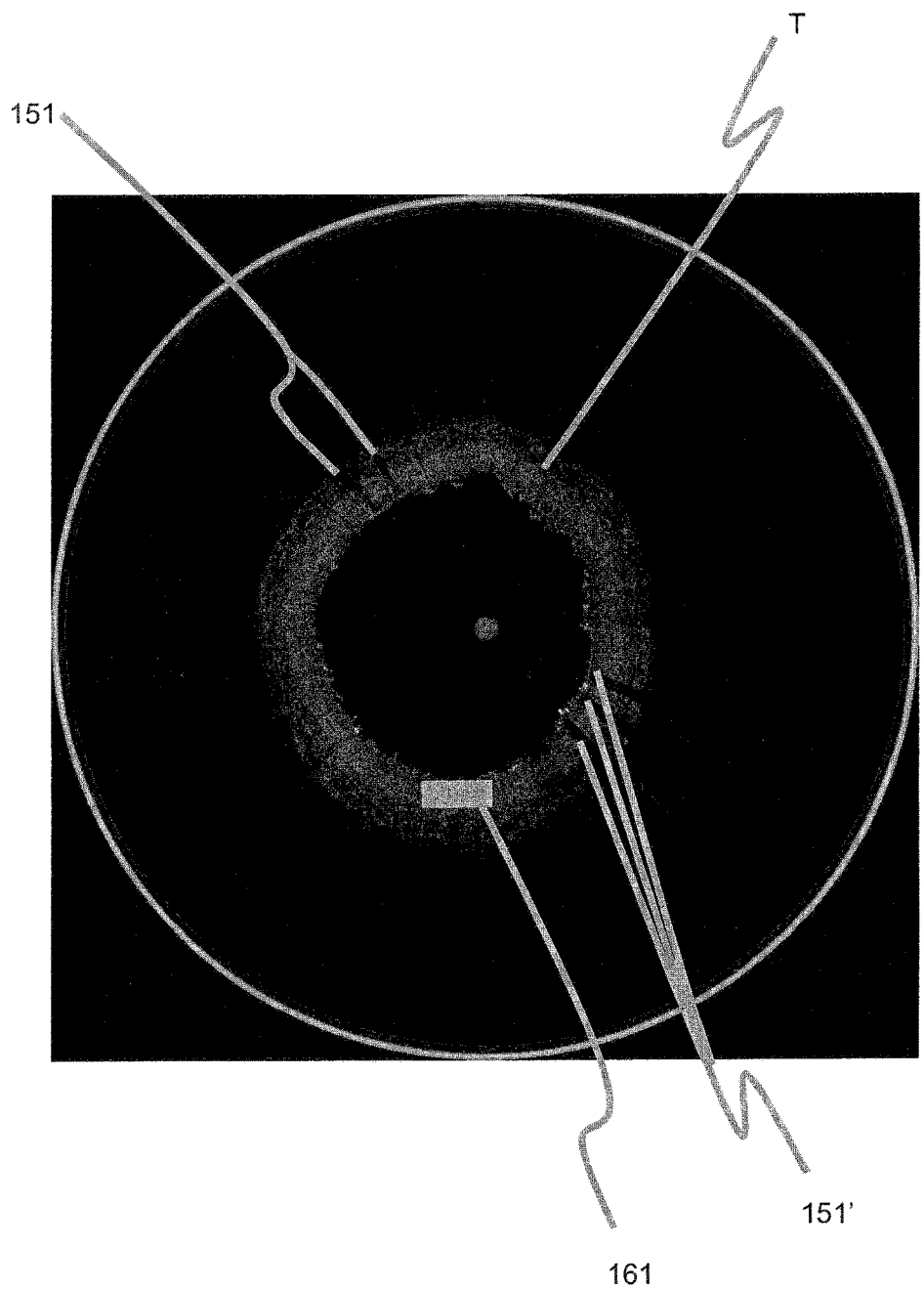
FIG. 4 is an image produced by the imaging system of FIG. 1.

The image shown in FIG. 4 may represent an OCT image, such as, for example, a single slice image provided by OCT device 100. The image includes data representing Tissue T, as well as data representing a first marker 151 comprising two linear elements and data representing a second marker 151' comprising three linear elements. Also shown is data representing a tissue marker 161. The image shown in FIG. 4 can be registered to a second image, such as a second OCT image or an image from a visible light camera positioned in an endoscope, for example, the image shown in FIG. 2. The second image may include a representation of one or more of tissue marker 161, marker 151 or marker 151', such that the one or more representations allow rotational registration of the second image to the first image.

Figure 5:
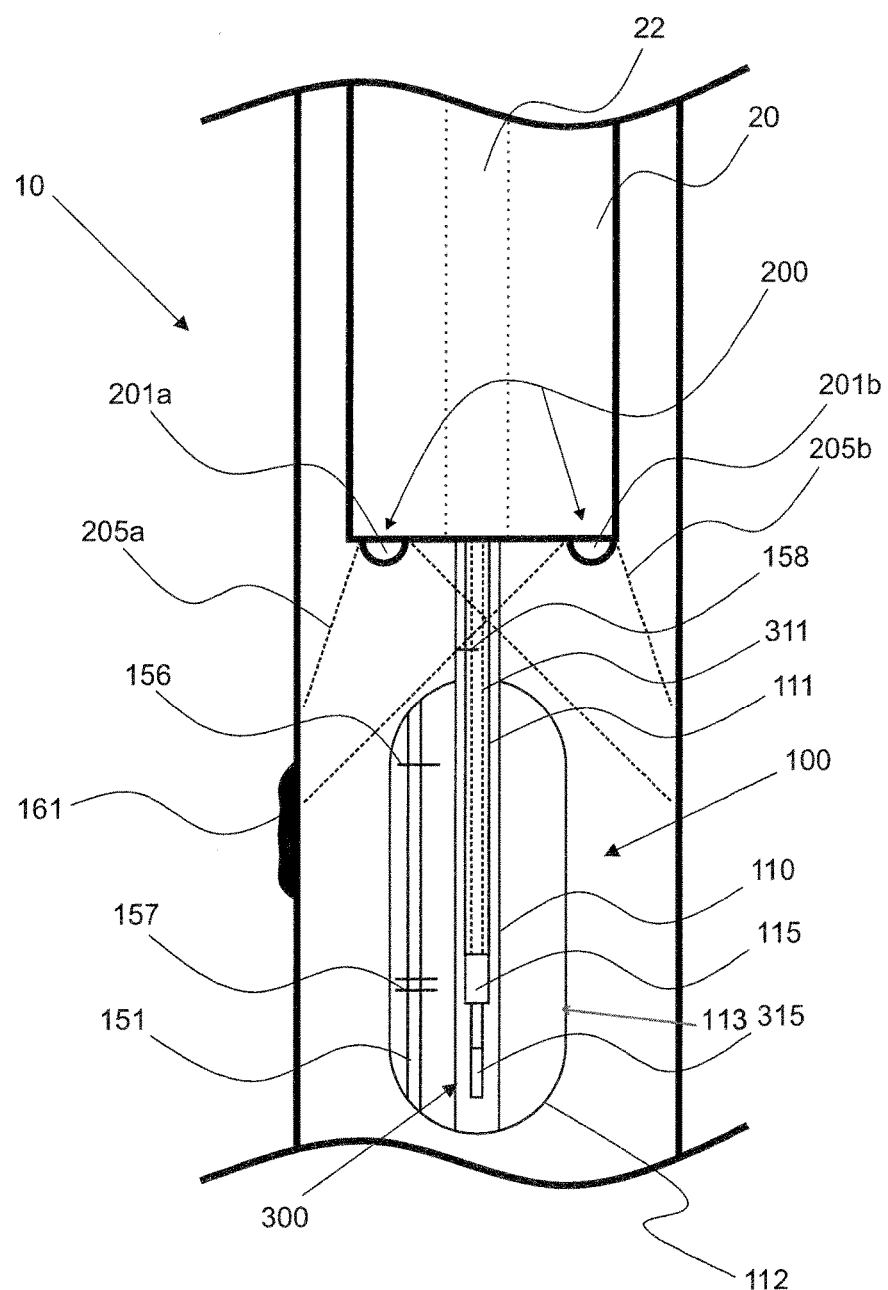
FIG. 5 is a side view of components of an imaging system, in accordance with the principles of the present disclosure.

In FIG. 5, a side view of a distal portion of an imaging system comprising registration marks and three imaging devices is illustrated. System 10 includes an endoscope 20, a first imaging device 200, e.g. a stereoscopic camera, a second imaging device 100, e.g. a OCT device, and a third imaging device 300, e.g. an ultrasound imager. Stereoscopic camera 200 including lenses 201a and 201b, includes fields of view 205a and 205b, respectively. OCT device 100 is constructed and arranged to produce an OCT image. OCT device 100 includes an elongate shaft 110, which has been slidingly passed through working channel 22 of endoscope 20. OCT device 100 includes balloon 112 of similar construction to balloon 112 of FIG. 1. Balloon 112 includes registration markers 151, 156, 157, 158 and 161, surface configuration 162, second portion 164 and fiber 165. Other configurations can replace balloon 112 with a shaft/catheter, as described above. OCT device 100 includes inner member 111 with distally mounted imaging assembly 115. Imaging assembly 115 is configured similar to imaging assembly 115 of FIG. 1, such as to produce a two-dimensional image of the plane orthogonal to a rotating imaging assembly 115. Imaging assembly 115 may be configured to both rotate and translate such as to produce a three-dimensional image comprising a series of slice images.

Ultrasound imager 300 includes shaft 311 and ultrasound crystal 315. Inner member 111 of OCT device 100 includes an inner shaft through which shaft 311 is slidingly received. In an alternative embodiment, inner member 111 and shaft 311 are positioned in a side by side configuration. In another alternative embodiment, inner member 111 comprises shaft 311, such that imaging assembly 115 and ultrasound crystal 315 are mounted to a single shaft, such as a shaft comprising a fiber optic cable and one or more electrical wires.

At the distal end of shaft 311 is ultrasound crystal 315, configured to transmit and receive ultrasound waves, such as to produce a two-dimensional image of the plane orthogonal to crystal 315. Similar to the image creation of imaging assembly 115, crystal 315 is constructed and arranged to produce a two-dimensional image of the plane orthogonal to a rotating crystal 315. Crystal 315 may be configured to both rotate and translate, such as to produce a three dimensional image comprising a series of slice images. Rotation of shaft 311 may be in the same direction as the rotation of inner member 111 or in the opposite direction, such as to prevent undesired twisting.

System 10 of FIG. 5 includes one or more markers 151, 156, 157, 158 and 161, typically of similar construction and placement as the markers with the same reference numbers described hereabove with reference to FIG. 1. In addition, markers 151, 156, 157 and/or 161 may be configured to be distinguishable in an ultrasound image produced by ultrasound imager 300, such as when markers 151, 156, 157 and/or 161 are configured to absorb, reflect and/or scatter ultrasonic waves.

Figure 6A:
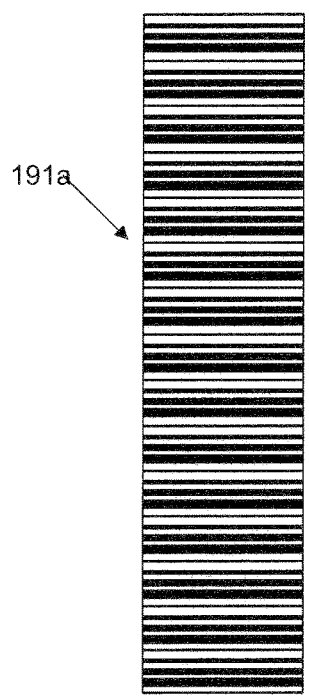
FIG. 6a is a side view of registration marks in accordance with the principles of the present disclosure.
Figure 6B:
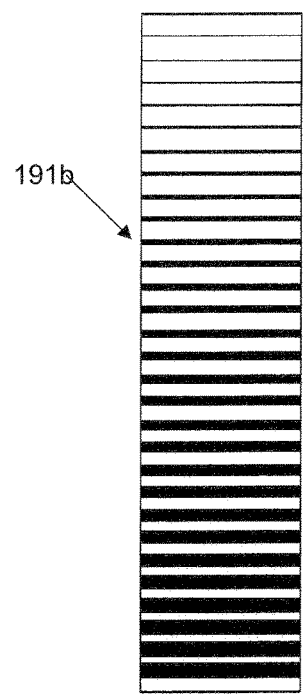
FIG. 6b is a side view of registration marks in accordance with the principles of the present disclosure.
Figure 6C:
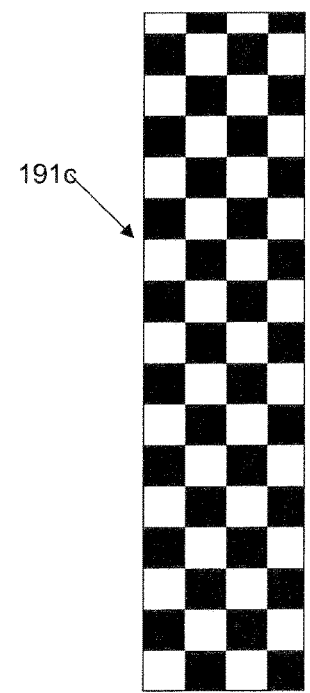
FIG. 6c is a side view of registration marks in accordance with the principles of the present disclosure.

As shown in FIGS. 6a-6c, numerous configurations of registration patterns may embedded into balloon 112 as the circumferential registration pattern 191. Various configurations of series of monochromatic or varying chroma shapes, such as lines, can be used to indicate rotational orientation or displacement of an optical pathway and/or a prismatic mirror, due to the fixed alignment with a beam splitter and the optical pathway. These configurations can be employed to indicate absolute as well as differential rotational orientation, such as those used in optical encoder registration patterns known to those of skill in the art. In the configuration shown in FIG. 6a, circumferential registration pattern 191a comprises multiple sets of repeated patterns of increasing width lines, such as to indicate a differential rotational orientation. In the configuration shown in FIG. 6B, circumferential registration pattern 191b comprises a single series of increasing width lines such as to indicate an absolute rotational orientation.

The registration patterns of FIGS. 6a and 6b provide radial registration information, such as when a prismatic mirror is receiving reflections of light from tissue T while rotating, similar to the information received from registration mark 151 of FIG. 1. Circumferential registration pattern 191c shown in FIG. 6c, provides both radial and longitudinal information, such as the information provided by the combination of markers 151 and 156 and/or 157 described hereabove.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A system for registering images, comprising:
a first imaging device comprising a body having a first channel and a second channel, said first channel having an imager slidably disposed therein, said first image device configured to produce a first image of a body cavity; and
an imaging system comprising:
a second imaging device having a shaft slidably disposed within said second channel and an imager having a distal tip that is positioned within the shaft, said imager of said second imaging device being configured to be positioned approximate to said imager of said first imaging device within said body cavity and configured to produce a second image, and
an elongated member having an inner surface defining a cavity and an outer surface, a distal end surface of the shaft being coupled to the inner surface, wherein the elongated member is molded to include imaging markers such that said imaging markers are embedded within the outer surface, wherein at least one of the image markers is configured to produce registration information in the first image and the second image, and wherein at least one of said image markers is radiopaque.

2. A system as recited in claim 1, wherein the elongated member is a medical balloon that is movable between a collapsed configuration and an expanded configuration.

3. A system as recited in claim 1, wherein at least one of the image markers comprises Polyethylene terephthalate (PET).

4. A system as recited in claim 1, wherein at least one of the image markers is anti-reflective.

5. A system as recited in claim 1, wherein at least one of the image markers is embedded in the outer surface.

6. A system as recited in claim 1, wherein at least one of the image markers is configured to absorb, reflect or scatter electromagnetic radiation.

7. A system as recited in claim 1, wherein at least one of the image markers is configured to absorb, reflect or scatter ultrasound.

8. A system as recited in claim 1, wherein at least one of the image markers comprises a wire, a metal foil, a metal strip, a photovoltaic fiber, an ink, a dye, or a combination thereof.

9. A method for registering images using the system for registering images in claim 1, comprising the steps of:
inserting said first imaging device into a cavity of a patient;
inserting said imaging system positioned with said elongated member into the cavity of the patient;
producing by said first imaging device a first image containing an image of at least one marker;
producing by said second imaging device a second image containing an image of said marker; and
registering said first image and said second image based on the image of the marker in the first and second images.

10. A method as recited in claim 9, wherein the at least one marker is embedded in the surface of the elongated member.

11. A method as recited in claim 10, wherein the at least one marker comprises a wire, a metal foil, a metal strip, a photovoltaic fiber, an ink, a dye, or a combination thereof.

12. A method as recited in claim 9, wherein the at least one marker is tissue of the patient.

13. A method as recited in claim 12, further comprising dying the tissue of the patient to create the at least one marker.

14. A method as recited in claim 9, wherein the first and second images are produced simultaneously.

15. A system as recited in claim 1, wherein the second channel is coaxial with a longitudinal axis defined by the body and the first channel is offset from the longitudinal axis.

16. A system for registering images, comprising:
a first imaging device comprising a body having a first channel and a second channel, said first channel having an imager slidably disposed therein, said first image device configured to produce a first image of a body cavity; and
an imaging system comprising:
a second imaging device having a shaft slidably disposed within said second channel and an imager movably positioned within the shaft and configured to be positioned approximate to said imager of said first imaging device within said body cavity and configured to produce a second image, and an elongated member having an inner surface and an outer surface defining a non-uniform profile, said elongated member comprising a proximal end that is coupled to a proximal end of said shaft and a distal end that is coupled to a distal end of said shaft such that a distal end surface of the shaft is coupled to the inner surface to prevent the imager of the second imaging device from moving distal to the distal end of said elongated member, the outer surface including at least one surface feature such that the profile is non-uniform, wherein the surface feature is viewable in the first image and the second image to produce registration information.

17. A system as recited in claim 16, wherein the at least one surface feature is a recess.

18. A system as recited in claim 16, wherein the at least one surface feature includes a plurality of spaced apart recesses.

19. A system as recited in claim 16, wherein the at least one surface feature is a protrusion.

20. A system as recited in claim 16, wherein the elongated member is pre-formed to have the non-uniform profile.

\* \* \* \* \*